United States Patent [19]

Sekita et al.

[11] Patent Number: 5,105,661
[45] Date of Patent: Apr. 21, 1992

[54] METHOD OF DETECTING A LEVEL OF LIQUID IN A MOVING CYLINDRICAL BODY

[75] Inventors: Takuo Sekita, Niihari; Takashi Abe, Iwaki, both of Japan

[73] Assignee: Kureha Chemical Industry Company, Limited, Tokyo, Japan

[21] Appl. No.: 632,124

[22] Filed: Dec. 21, 1990

[30] Foreign Application Priority Data

Dec. 28, 1989 [JP] Japan .................. 1-150953[U]

[51] Int. Cl.$^5$ .................. G01N 29/02; G01F 23/28
[52] U.S. Cl. .................. 73/290 V; 141/95; 264/40.4
[58] Field of Search .............. 73/290 V, 644; 141/83; 340/621; 264/40.4, 559; 425/135, 169

[56] References Cited

U.S. PATENT DOCUMENTS

| | | | |
|---|---|---|---|
| 3,102,301 | 9/1963 | Dechene | 264/40.4 |
| 3,745,833 | 7/1973 | Armstrong | 73/644 |
| 3,927,569 | 12/1975 | Bergdahl et al. | 73/290 V |
| 4,203,942 | 5/1980 | Sims, Jr. et al. | 264/559 |
| 4,302,623 | 11/1981 | Canfield | 73/290 V |
| 4,679,430 | 7/1987 | Scott-Kestin et al. | 73/290 V |
| 4,976,149 | 12/1990 | Ichikawa et al. | 73/644 |
| 4,978,484 | 12/1990 | Takashige et al. | 264/40.2 |

FOREIGN PATENT DOCUMENTS 2177510  1/1987 United Kingdom ............ 73/290 V

OTHER PUBLICATIONS

Chemical Engineers' Handbook, 5th Ed., Perry et al "Sonic Methods" (Copy AU 135), TP 155 p. 4, (pp. 22–47).

Primary Examiner—Daniel M. Yasich
Attorney, Agent, or Firm—Koda and Androlia

[57] ABSTRACT

A detection method of a liquid level supplies fluid between a moving cylindrical body such as a parison in a film manufacturing process and an ultrasonic transmitter and receiver or an ultrasonic transmitter-receiver opposite to an outer surface of the cylindrical body to keep acoustic contact between an ultrasonic vibration member and the cylindrical body through the fluid. A level of liquid in the cylindrical body is measured on the basis of whether ultrasonic propagating in the fluid and the liquid in the cylindrical body can be received with a predetermined signal level or not. Since the ultrasonic vibration member is brought into contact with the cylindrical body through the fluid, and the contact state therebetween is kept good, and wear, flaw, deformation, frictional heat or the like is not given to the cylindrical body. Further, even if the surface of the cylindrical body is rugged, good contact can be kept.

6 Claims, 4 Drawing Sheets

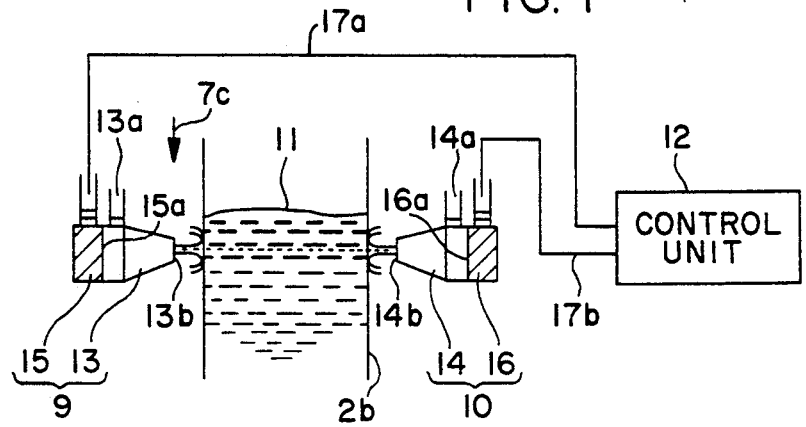
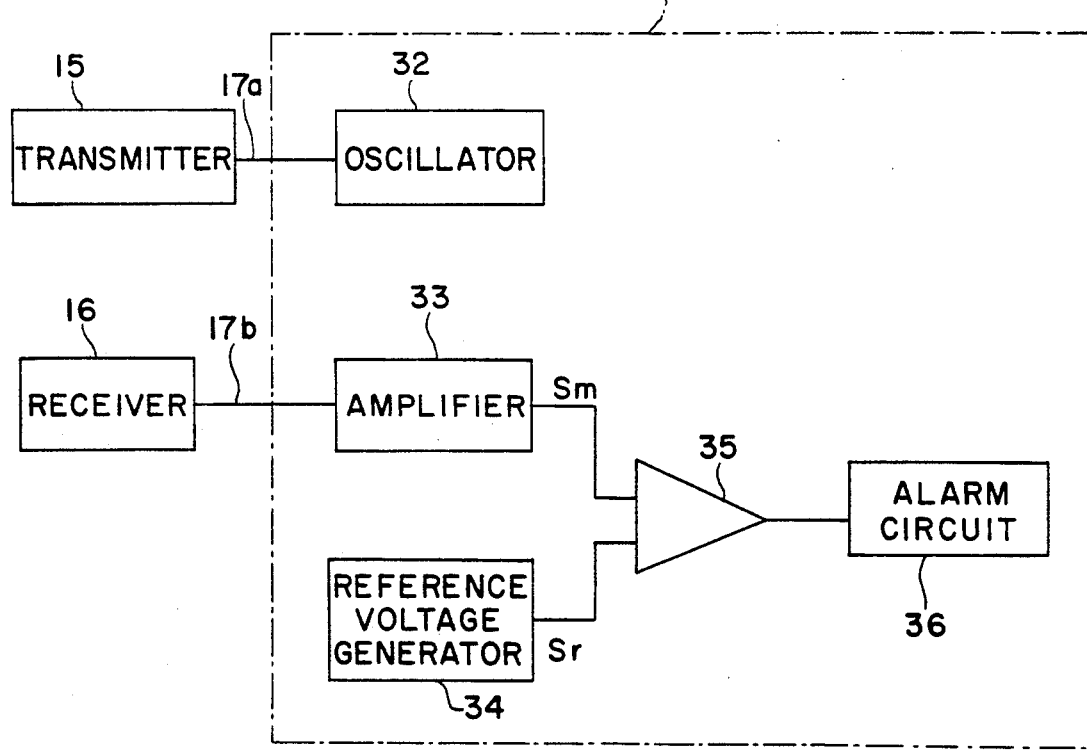

METHOD OF DETECTING A LEVEL OF LIQUID IN A MOVING CYLINDRICAL BODY

BACKGROUND OF THE INVENTION

The present invention relates to a detecting method of a level of liquid in a cylindrical body, which can detect a level of liquid in a moving cylindrical body with high accuracy without direct contact of a ultrasonic transmitter and receiver with the surface of the cylindrical body.

When a liquid level or the like is detected by an ultrasonic probe, it is necessary to keep acoustically good contact between the surface of an object to be examined and an ultrasonic transmitter and/or receiver without an air layer or air bubbles. The reason is that detection of the ultrasonic is remarkably impeded due to a phenomenon such as absorption or scattering of a sound wave when the air layer or air bubbles are present in a propagation path of the sound wave.

The ultrasonic probe includes a vibration material for transmitting or receiving the ultrasonic and a contact means disposed in a propagation path to make the acoustic contact between the vibration material and the object to be examined.

As a conventional structure of the ultrasonic probe, there are known a type including contact means formed into various shapes and made of synthetic resin or metal in accordance with shapes and properties, and a type including a rubber balloon filled with liquid and disposed in front of a transmitting or receiving plane of ultrasonic to use it as the contact means.

However, the ultrasonic probe provided with the conventional contact means of synthetic resin or metal has a drawback that the object to be examined such as a moving object, an easily injured object or a flexible or soft object such as film is given wear, flaw, deformation, frictional heat or the like. Further, the ultrasonic probe equipped with the rubber balloon as the contact means has a problem that the flexible object such as film is pressed excessively and further the contact means can not come into contact with an object having a rugged surface sufficiently.

In a film manufacturing process, a pile agent is pushed out from an extruder to fill a parison in a cooling process with the pile agent, while it is necessary to detect a liquid surface of the filled pile agent. The detection and control of the liquid surface of the pile agent are required to stabilize a pressure within the parison, uniform a thickness of the parison and improve the quality of film manufactured from the parison. For example, when the conventional ultrasonic probe is used for the detection of the liquid surface, the parison in the cooling process is injured and deformed excessively. Accordingly, when the parison is expanded by the inflation method to manufacture a film product, the quality of the film product is degraded.

Further, a detecting apparatus of a liquid surface without contact involves a photoelectric liquid surface detecting apparatus. However, when this detecting apparatus is to detect the liquid surface in the parison, cooling water flowing along an outer periphery of the parison impedes transmission of light to thereby detect the liquid surface in error, and further when the parison is opaque, detection itself is impossible.

It is an object of the present invention to provide a liquid level detection method capable of detecting a level of liquid in a soft and moving cylindrical object to be examined such as an extruded parison in a cooling process with high accuracy.

SUMMARY OF THE INVENTION

According to the present invention, an ultrasonic probe is disposed outside of a moving cylindrical body such as a parison in a cooling process of a film manufacturing process so as not to be in contact with the cylindrical body and flowing water is supplied along the propagation direction of ultrasonic in space between a vibration member of the probe and an outer surface of the cylindrical body so that the fluid keeps acoustic contact between the ultrasonic probe and the cylindrical body sufficiently.

BRIEF DESCRIPTION OF THE DRAWINGS

FIG. 1 schematically illustrates a liquid level detection method according to the present invention;

FIG. 2 is a circuit block diagram showing an example of a controller in the detecting apparatus of FIG. 1;

DETAILED DESCRIPTION OF PREFERRED EMBODIMENT

In the present invention, a fluid flows along a propagation direction of ultrasonic between a vibration plane of an ultrasonic transmitter or an ultrasonic receiver and a moving cylindrical body (hereinafter merely referred to as a cylindrical body) such as a parison in a film manufacturing process. Accordingly, good acoustic contact can be kept between the vibration plane and the cylindrical body through the fluid. Further, since the contact therebetween is made through the fluid, the contact is soft for the cylindrical body and there is no apprehension that wear, flaw, deformation, frictional heat or the like is not given to the cylindrical body. In addition, even if the surface of the cylindrical body is rugged, good acoustic contact is effected. Accordingly, the liquid surface is detected with high accuracy.

Figure 5:
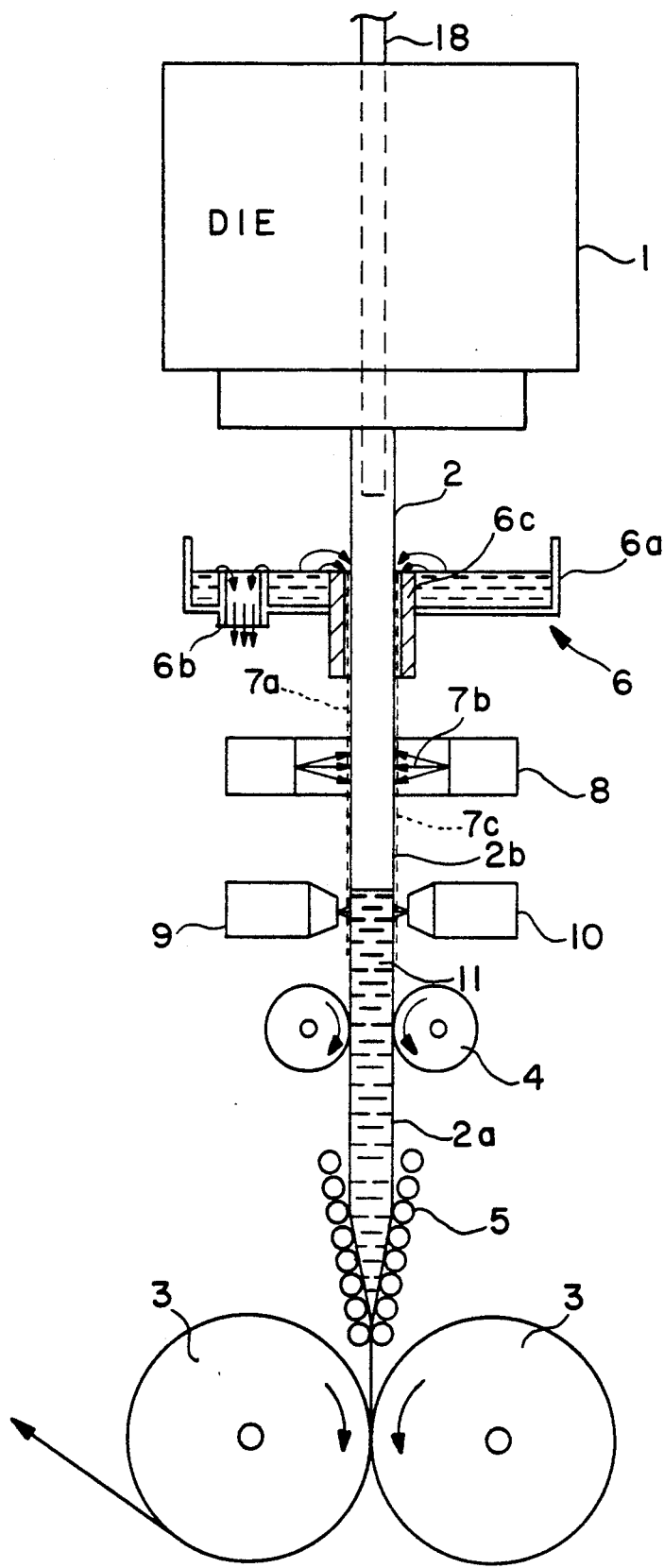
FIG. 5 is a partial front view schematically illustrating a parison molding process of a manufacture of film of synthetic resin as an application example of a liquid level detection method according to the present invention.

Referring to FIG. 5, a parison molding process is now described.

In FIG. 5, numeral 1 denotes a die for extruding thermoplastic resin such as PVDC (vinylidene chloride resin) which is melted by heating, 2 melted resin extruded from the die 1 into a hollow cylindrical shape, 2a a parison formed by cooling the melted resin in the form of cylinder, 2b a parison on the way of cooling process, 3 a pair of taking-over rollers for holding the parison 2a therebetween to transport it to a next air suction process (not shown), 4 a pair of guide rollers for guiding the progression of the parison 2a downward of the figure (toward the taking-over rollers 3), and 5 a group of guide rollers disposed in substantially V-shape to deform the parison 2a into a flat or compressed shape so that the pair of taking-over rollers 3 tend to hold the parison 2a therebetween.

Numeral 6 denotes a fluid supply portion disposed under the die 1 to form a flowing water layer 7a around an outer periphery of the cylindrical melted resin 2 uniformly. The fluid supply portion 6 includes a reservoir 6a and a cylindrical dam 6c disposed to surround the outer periphery of the cylindrical melted resin 2 with a fixed space from the outer periphery of the melted resin 2. The surface of liquid in the reservoir 6a is always kept to a fixed level by means of an overflow tube 6b. The fluid exceeding the dam 6c and overflowing from the reservoir 6a flows down on the outer periphery of the melted resin 2 to form the flowing water layer 7a. Further, it is desirable that a cooling ring 8 is disposed under the fluid supply portion 6 to sprinkle cooling water 7b on the outer periphery of the cylindrical melted resin 2 like a shower and further facilitate the cooling of the melted resin 2.

In FIG. 5, numerals 9 and 10 denote ultrasonic probes, 9 a transmitting probe and 10 a receiving probe. The transmitting probe 9 is opposite to a wall of the parison 2b in the outside of the parison 2b in the cooling process. The receiving probe 2b is also opposite to the wall of the parison 2b from the opposite side of the transmitting probe 9. Thus, the transmitting probe 9 is opposite to the receiving probe 10 while the parison 2b is placed between the probes 9 and 10. The height of the probes 9 and 10 is established so that a propagation path of ultrasonic produced from the transmitting probe 9 passes through liquid 11 in the parison 2b when a surface of the liquid 11 poured into the parison 2b through the inside of the die 1 is a reference level or more. More particularly, it can be detected whether the liquid 11 in the parison 2b exists in the propagation path of ultrasonic between the transmitting probe 9 and the receiving probe 10 or not.

The parison 2a which has been cooled is squeezed into a compressed shape by the taking-out rollers 3 and is transported to the next process. When the parison is squeezed, the liquid 11 is held little by little into a space formed between inner opposite surfaces of the parison 2a compressed to be brought into contact with each other so that the liquid 11 is supplied to the inside of the parison. Further, the liquid 11 held in the parison 2a is consumed as the parison 2a is taken down. Thus, the surface of the liquid 11 in the parisons 2a and 2b is lowered by an amount of the liquid 11 consumed when the parison 2a is taken down.

The level of ultrasonic received by the receiving probe 10 is reduced since the propagation path is cut off by an air layer when the liquid surface is deviated down from the propagation path of ultrasonic. Consequently, lowering of the surface of the liquid 11 in the parison can be detected. When the lowering of the surface of the liquid 11 is detected by an output of the receiving probe 10, a liquid supply means 18 is operated to supplement the liquid 11 into the parison.

A detection apparatus including the transmitting probe 9 and the receiving probe 10 is now described with reference to FIG. 1.

The present invention is described by taking the detection of liquid surface in the parison molding process shown in FIG. 5 as an example, while the present invention is not restricted by this example.

In FIG. 1, numeral 15 denotes a transmitter for producing ultrasonic, 16 a receiver for receiving ultrasonic transmitted through the liquid 11 in the parison 2b, and 12 a control unit for controlling operation of the transmitter 15 and the receiver 16. The transmitter 15 and the receiver 16 include a vibrating element constituted of a magnetostrictive element, an electrostrictive element or a piezoelectric element and a crystal vibrating element is exemplified by way of example.

Numerals 13 and 14 denote contact means for effecting acoustic contact between the transmitter 15 and the outer surface of the parison 2b on the way of cooling and between the receiver 16 and the outer surface of the parison 2b. The transmitting contact means 13 and the receiving contact means 14 have the same structure and include fluid supply inlets 13a and 14a and nozzles 13b and 14b, respectively. Fluid such as, for example, water supplied to vibration planes 15a and 16a of the transmitter 15 and the receiver 16 from the fluid supply inlets 13a and 14a of the contact means 13 and 14, respectively, flows along the propagation path of ultrasonic and is spouted from the nozzles 13b and 14b so that the fluid strikes on the outer surface of the parison 2b opposite to the nozzles 13b and 14b. The nozzles 13b and 14b serve to spout the fluid being in contact with the vibration surfaces 15a and 16a in the direction parallel to the propagation direction of ultrasonic. Consequently, the acoustic contact is completed between the transmitter 15 and the receiver 16 and the outer surface of the parison 2b through the fluid.

In the embodiment, a combination of the transmitter 15 and the contact means 13 and a combination of the receiver 16 and the contact means 14 are named an ultrasonic probe. In the above description, the transmitting probe 9 and the receiving probe 10 have the same structure but may have different structures.

A speed of the fluid spouted from the nozzles 13b and 14b is properly selected in accordance with a moving speed, rigidity and ruggedness of the surface of an object to be examined, a distance between the probe and the object and the like, while the speed is generally 1 cm/sec to 5 m/sec and preferably 3 cm/sec to 3 m/sec. When the speed of fluid is lower than 1 cm/sec, it is necessary to place the probe nearer to the object than it needs and there is a large possibility that the probe comes into contact with the moving object due to movement of the object. Further, when the speed of fluid exceeds 5 m/sec, the pressure of fluid applied to the object can not be neglected and when the object is a cylindrical body made of soft material, the object is deformed by the pressure of fluid and the level of liquid 11 in the object can not be detected exactly.

A circuit configuration of the control unit 12 is now described with reference to FIG. 2.

An oscillator 32 in FIG. 2 supplies electric energy having a frequency corresponding to a frequency of ultrasonic to a vibrating element constituting the transmitter 15. The vibrating element constituting the transmitter 15 converts the electric energy supplied through a transmitting cable 17a into mechanical vibration to thereby produce ultrasonic. The oscillator 32 may oscillate with a frequency selected from a frequency band in the ultrasonic range and a frequency of several tens to several hundreds KHz is usually used.

On the other hand, the ultrasonic passing through the parison 2b constituting the object to strike on the receiving contact means 14 gives sound pressure corresponding to a strength of the ultrasonic to the vibrating element constituting the receiver 16 to be converted into electric energy by the vibrating element and be produced as a received signal. The received signal is supplied to an amplifier 33 in the control unit 12 through a receiving cable 17b. Further, a comparator 35 in the control unit 12 compares a reference voltage Sr from a reference voltage generator 34 with the received signal Sm amplified by the amplifier 33. As a result of the comparison, if Sm>Sr, a low Transistor-Transistor Logic (TTL) level signal is supplied to an alarm circuit 36 and if Sm<Sr, a high TTL-level signal is supplied to the alarm circuit 36. The alarm circuit 36 opens and closes a solid state relay (SSR) of, for example, TTL-driven type in response to the TTL signal. Supply means for the liquid 11 is operated in response to the opening and closing of the SSR in the parison molding process of FIG. 5 to supply a predetermined amount of liquid 11 into the parison. Further, an alarm lamp indicating that the liquid level of the liquid 11 is lowered is turned on at need, or an alarm is sounded to inform the operator of the lowering of the level of the liquid 11.

A detection method of a level of the liquid 11, in the parison using the detection apparatus constructed above is now described.

FIG. 1 shows a case where the level of the liquid 11 in the parison 2b which is the object to be examined is higher than the reference level. The ultrasonic produced from the transmitter 15 of the transmitting probe 9 with a predetermined frequency continuously or intermittently propagates in the fluid such as water supplied in the contact means 13 to be spouted from the nozzle toward the parison and further in the cooling fluid spouted onto or flowing on the outer surface of the parison 2b and then propagates in the liquid 11 in the parison 2b. The ultrasonic then propagates in the fluid spouted from the contact means 14 of the receiving probe 10 and in the cooling fluid to be received by the receiver 16. The received signal is amplified by the amplifier 33. In the state of FIG. 1, since there is no boundary of the air layer between the transmitter 15 and the receiver 16, the ultrasonic is received by the receiver 16 without substantially scattering or reflection and without remarkable attenuation of energy of sound wave thereof. Accordingly, the received and amplified signal Sm is larger than the reference voltage Sr, and Sm>Sr in the comparison of the comparator 35 so that the TTL level thereof is "0".

As described above, when the liquid 11 is consumed by feeding of the parison by the taking-over rollers and the level of the liquid 11 is lowered from the reference level, an air layer is formed in the propagation path of ultrasonic produced from the the transmitter 15. Since the ultrasonic is scattered or reflected by the air layer, the sound wave energy received by the receiver 16 at this time is remarkably attenuated. Accordingly, the received signal Sm amplified by the amplifier 33 in the control unit 12 of FIG. 2 is smaller than the reference voltage Sr and accordingly Sm<Sr in the comparison of the comparator 35 so that the TTL signal "1" is produced. The TTL signal operates the SSR of the alarm circuit 36 to operate the liquid supply means for a predetermined time so that the liquid 11 is supplemented and the level of the liquid 11 in the parison is recovered to the reference level or more.

In order to attain the above operation by the control unit 12, it is necessary that the reference voltage Sr produced from the reference voltage generator 34 is set to be smaller than the high level received and amplified signal Sm when the liquid 11 is in the propagation path of ultrasonic and be larger than the low level received and amplified signal Sm when the air layer exists within the parison 2b in the propagation path of ultrasonic.

Figure 3:
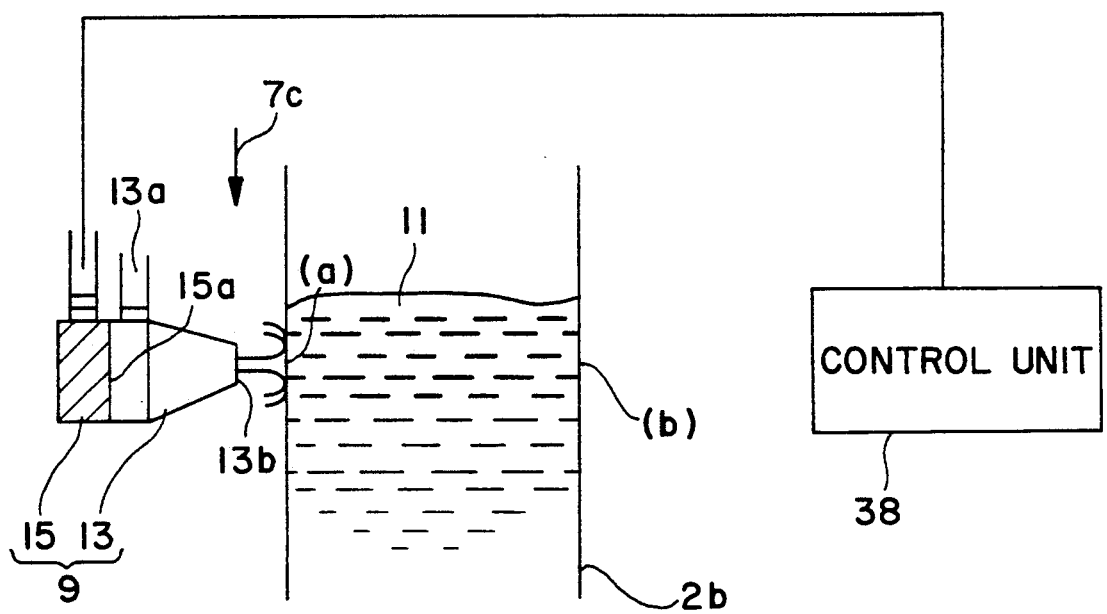
FIG. 3 schematically illustrates another liquid level detection method.

FIG. 3 shows another embodiment of the detection method of a liquid level in the cylindrical body according to the present invention.

The embodiment uses a so-called impulse reflection method and the ultrasonic probe 9 is opposite to only one wall of the parison 2b. The ultrasonic probe 9 is used for transmitting and receiving of ultrasonic. The probe 9 has the same structure as that used as the transmitting probe in FIG. 1 and the fluid is spouted from the nozzle 13b of the probe 13 toward the outer surface of the parison 2b. Thus, the acoustic contact is formed between the transmitter-receiver 15 used as the transmitting unit and the receiving unit and the wall of the parison 2b through the fluid.

Ultrasonic is produced as short-duration impulses from the transmitter-receiver 15 under the control of the control unit 38 connected to the ultrasonic probe 9. In FIG. 3, since the level of the liquid 11 in the parison 2b is higher than the reference level, the ultrasonic produced as the impulses from the transmitter-receiver 15 propagates in the fluid spouted from the contact means 13 and further in the liquid 11 and reaches the wall designated by (b) of the parison 2b. Since a boundary is formed between the wall designated by (b) and the air layer outside of the wall, the ultrasonic produced as the impulses is reflected by the wall designated by (b) and echoes thereof are received by the transmitter-receiver 15. Further, when the level of the liquid 11 in the parison 2b is lower than the reference level, the air layer is formed at a portion in the parison 2b corresponding to the propagation path of the ultrasonic and a boundary is formed between a wall designated by (a) and the air layer. Accordingly, the ultrasonic produced as the impulses is reflected by the wall designated by (a) and echoes thereof are received by the transmitter-receiver 15. Accordingly, an echo received time is measured taking an impulse produced time of the transmitter-receiver 15 as a reference and whether the liquid 11 exists in the propagation path of ultrasonic or not, that is, whether the level of the liquid 11 is higher than the reference level or not can be detected on the basis of a difference between the echo received time and the impulse produced time.

Figure 4A:
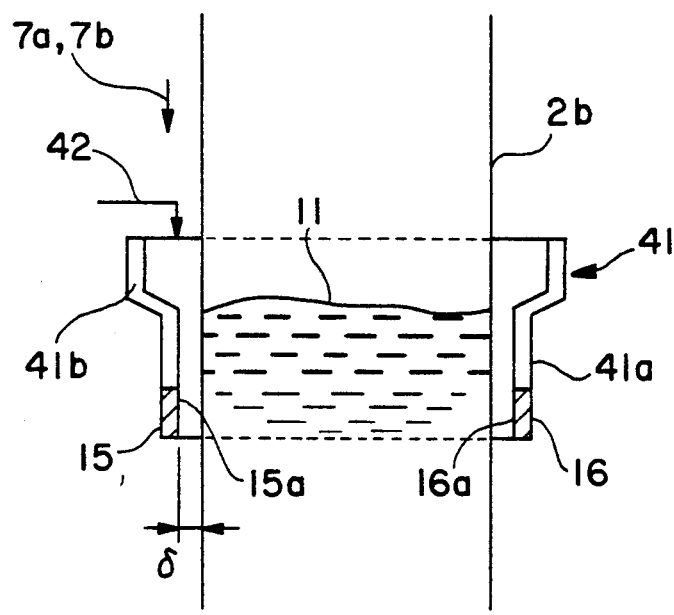
FIGS. 4A and 4B schematically illustrate still another liquid level detection method.
Figure 4B:
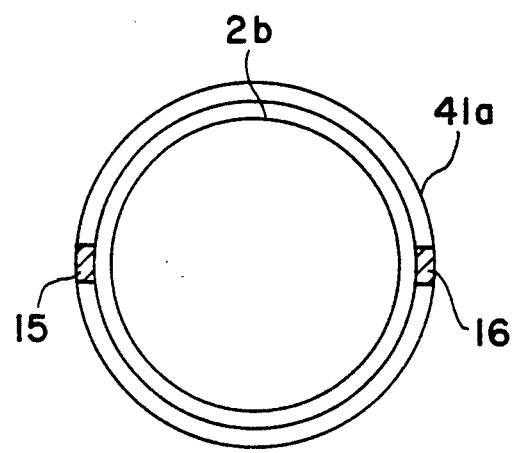

FIG. 4 shows still another embodiment of a detection method of a liquid level in a cylindrical body. FIG. 4(A) schematically illustrates the detection of a liquid level and FIG. 4(B) is a bottom view of an ultrasonic probe used in the detection of FIG. 4(A).

In the embodiment, the contact means 41 is formed into a ring and is disposed to surround the outer periphery of the parison 2b which is the object to be examined. An inner diameter of a lower portion of the contact means 41 is small. The lower portion of the contact means having the small inner diameter constitutes a water film forming portion 41a, and a space δ between the water film forming portion 41a and the wall of the parison 2b is made small, so that thin and uniform water film is formed on the outer periphery of the parison 2b. A transmitter 15 and a receiver 16 opposed each other through the parison 2b are held in the water film forming portion 41a. The transmitter 15 and the receiver 16 are the substantially same as those shown in FIG. 1 and the same control unit as that of FIG. 2 is also used.

The flowing water layer 7a and the cooling water 7b shown in FIG. 5 flow into a water receiver 41b of the contact means 41 and are gathered into the water film forming portion 41a having the small diameter so that the water film having a fixed thickness is formed between the water film forming portion 41a and the wall of the parison 2b. The water film is stable flow of water without deviation and production of air bubbles in the water film is suppressed. Accordingly, the ultrasonic produced continuously (or intermittently) from the transmitter 15 propagates in the water film. When the level of the liquid 11 in the parison 2b is higher than the reference level, the ultrasonic further propagates in the liquid 11 and is received by the receiver 16 through the water film. Further, when the level of the liquid 11 is lower than the reference level, an air layer is formed in the parison 2b constituting the propagation path of ultrasonic, so that sound wave energy received by the receiver 16 is remarkably attenuated. Thus, the received signal is compared with the reference voltage in the same controller as that of FIG. 2 and whether the level of the liquid 11 in the parison is higher than the reference level or not is detected.

In the above description, the flowing water layer 7a and the cooling water 7b are used as fluid for forming the water film, while when supply means of such fluid is not used, the fluid 42 can be supplied from other fluid supply means to the water receiver 41b to form stable water film.

In the liquid level detection apparatus shown in FIG. 4, when the level of the liquid 11 is higher than the reference level and the water film is not formed between the outer surface of the parison 2b and the water film forming portion 41a, a level of the received signal of the receiver 16 is lowered. Accordingly, it can be detected from the lowering of the level of the received signal that the flowing water layer 7a and the cooling water 7b in the parison molding process shown in FIG. 5 are stopped. Further, reference voltages capable of identifying the received signal in the case where the level of the liquid 11 is lower and the water film is formed and the received signal in the case where the level of the liquid 11 is higher than the reference level and the water film is not formed can be set so that the control unit can distinguish the lowering of the liquid level of the liquid 11 from the stop of the flowing water layer 7a.

The contact means 14 shown in FIG. 4 is used and only the transmitter 15 is provided to be used as an ultrasonic transmitting and receiving member, so that the level of the liquid can be detected by the impulse reflection method as shown in FIG. 3.

As described above, when the probe 41 shown in FIG. 4 is used, since water flows in the vertical direction to the propagation direction of ultrasonic, pressure of water exerted on the surface of the object to be examined is reduced as compared with the probe 9 and detection for the object such as cylindrical film can be made with high accuracy.

The cylindrical body to which the liquid level detection method according to the present invention is applied is not limited to the parison in the cooling process as shown in FIG. 5. In a food packing field, the detection method according to the present invention can apply to detection of level of liquefied or paste-like food filled into a cylindrical resin film, detection of level of liquid filled into a plastic or glass container or the like.

Further, the detection method of the present invention is not limited to the detection of liquid level and is useful to measurement of an inner flaw or an outer diameter of a long object to examined which is continuously moved.

As described above, according to the present invention, since the fluid is supplied between the vibration plane of the transmitter, the receiver or the transmitter-receiver of ultrasonic and the cylindrical body to keep the acoustic contact, even if the cylindrical body tends to be injured or is soft, good acoustic contact can be kept without flaw and deformation and unnecessary frictional heat is not given to the cylindrical body. In addition, excessive pressure is not given to the cylindrical body and even if the surface of the cylindrical body is rugged, good acoustic contact can be kept. Even if the cylindrical body is opaque, a level of liquid in the cylindrical body can be detected.

Accordingly, the detection method of a liquid level in the cylindrical body according to the present invention can detect the liquid level with high accuracy regardless of various conditions.

I claim:

1. A method of detecting a level of liquid in a moving parison of a film manufacturing process, comprising disposing a transmitting ultrasonic probe outside of said moving parison formed by cooling a melted resin extruded from a die in the form of cylinder and a receiving ultrasonic probe outside of the moving parison from the opposite side of said transmitting ultrasonic probe without contact between the moving parison and said probes, supplying flowing water along a propagation direction of ultrasonic waves in a space between vibration member of said each proves and an outer surface of the moving parison so as to make acoustic contact between the moving parison and said probes, detecting whether the receiving ultrasonic probe receives ultrasonic waves produced from the transmitting ultrasonic probe passed through the liquid so that detecting whether the liquid in the moving parison exists in the propagation path of ultrasonic waves between the probes or not, and pouring the liquid into the parison through the inside of said die when the level of the liquid in the moving parison is lowered than said propagation path by an amount of the liquid consumed.

2. A method according to claim 1, wherein cooling fluid flows on an outer surface of said moving parison and the acoustic contact between said ultrasonic probe and the moving parison is maintained by said cooling fluid and said water flowing along the propagation direction of ultrasonic.

3. A method of detecting a level of liquid in a moving parison of a film manufacturing process, comprising disposing a ring ultrasonic probe around an outer periphery of said moving parison formed by cooling a melted resin extruded from a die in the form of cylinder, said ring probe having an inner surface in which an ultrasonic transmitter and an ultrasonic receiver opposed each other through the moving parison, supplying fluid in a space between the moving parison and the ring probe in a vertical direction to a propagation direction of ultrasonic waves so as to make acoustic contact between the cylindrical body and said transmitter and receiver, detecting whether the receiver receives ultrasonic waves produced from the transmitter passed through the liquid so that detecting whether the liquid in the moving parison exists in the propagation path of ultrasonic waves between the transmitter and receiver or not, and pouring the liquid into the parison through the inside of said die when the liquid surface of the liquid in the moving parison is lower than said propagation path by an amount of the liquid consumed.

4. A method according to claim 3, wherein the moving cylindrical body is a parison in a film manufacturing process and the fluid serves to cool said parison.

5. A method according to claim 3, wherein said ring ultrasonic probe includes a lower portion having a small inner diameter and a space between said lower portion and the moving cylindrical body is formed narrower, said ultrasonic vibration member being embedded in said lower portion having a small inner diameter.

6. A method of detecting a level of a liquid in a moving parison of a film manufacturing process, comprising disposing a transmitting and receiving ultrasonic probe out of only one wall of said moving parison formed by cooling a melted resin extruded from a die in the form of cylinder without contact between the moving parison and the probe, supplying flowing water along a propagation direction of ultrasonic waves in a space between a vibration member of said probe and an outer surface of the moving parison so as to make acoustic contact between the moving parison and the probe, measuring a time which the probe receives ultrasonic impulse echo produced from the probe itself so that detecting whether the liquid in the moving parison exists in the propagation path of ultrasonic waves or not, and pouring the liquid into the parison through the inside of said die when the level of the liquid in the moving parison is lower than said propagation path by an amount of the liquid consumed.

* * * * *